United States Patent [19]

Gullberg et al.

[11] Patent Number: 5,841,141

[45] Date of Patent: Nov. 24, 1998

[54] IMAGE RECONSTRUCTION FROM V-PROJECTIONS ACQUIRED BY COMPTON CAMERA

[75] Inventors: Grant T. Gullberg; Gengsheng Lawrence Zeng; Roman Basko, all of Salt Lake City, Utah

[73] Assignee: The University of Utah, Salt Lake City, Utah

[21] Appl. No.: 868,273

[22] Filed: Jun. 3, 1997

[51] Int. Cl.$^6$ .................................................. G01T 1/164
[52] U.S. Cl. ................. 250/363.04; 250/363.03
[58] Field of Search ................ 378/6, 87; 250/363.03, 250/363.04

[56] References Cited

U.S. PATENT DOCUMENTS

| | | |
|---|---|---|
| 4,055,765 | 10/1977 | Gerber et al. . |
| 4,185,274 | 1/1980 | Giallorenzi . |
| 4,437,007 | 3/1984 | Koslow et al. . |
| 4,529,882 | 7/1985 | Lee ........................................ 250/363.1 |
| 4,642,464 | 2/1987 | Mullani . |
| 4,833,327 | 5/1989 | Hart ..................................... 250/363.01 |
| 4,850,002 | 7/1989 | Harding et al. . |
| 4,857,723 | 8/1989 | Modisette . |
| 4,857,737 | 8/1989 | Kamae et al. . |
| 5,005,195 | 4/1991 | Lanza et al. . |
| 5,175,434 | 12/1992 | Engdahl . |
| 5,281,821 | 1/1994 | Antich et al. . |
| 5,334,839 | 8/1994 | Anderson et al. . |
| 5,457,321 | 10/1995 | Ichihara et al. ..................... 250/363.04 |
| 5,567,944 | 10/1996 | Rohe et al. .......................... 250/370.09 |
| 5,665,971 | 9/1997 | Chen et al. ........................... 250/385.1 |
| 5,742,056 | 4/1998 | Valentino et al. .................. 250/363.03 |

OTHER PUBLICATIONS

*Monte Carlo Study of a High Resolution Gamma Ray Telescope Used as a Polarimeter*, J. Park, et al., Workshop on High Resolution Gamma Ray Cosmology, UCLA, Nov. 2–3, 1988, © Elsevier Science Publishers B.V.

*Towards Direct Reconstruction from a Gamma Camera Based on Compton Scattering*, Michael J. Cree and Philip J. Bones, IEEE; Transactions on Medical Imaging; vol. 13, No. 2, Jun. 1994 IEEE.

*Primary Examiner*—Constantine Hannaher
*Attorney, Agent, or Firm*—Fay, Sharpe, Beall, Fagan, Minnich & McKee

[57] ABSTRACT

A SPECT system includes a Compton camera (14) disposed on a gantry (16). The camera (14) includes linear detectors (30a, 30b) operating without mechanical collimation for detecting radiation emanating from a subject to be imaged. A data processor (22) collects and processes radiation data in accordance with the detected radiation. Position and energy resolving circuitry (24) determines positions and energy deposited by photons striking the detectors. A projection generator (34) generates divergent projections or V-projections based on the collected data which determine a possible location of a gamma source of the detected radiation. A conversion processor (36) converts the V-projections into parallel projection data such as a Radon transformation. A reconstruction processor (38) reconstructs an image representation of a region of interest from the subject from the parallel projection data using filtered back projection. Alternately, two Compton cameras (70, 72) disposed at a selected angle to each other collect the radiation data and V-projections are generated from both cameras. A combination of V-projections are selected from both cameras and are converted into parallel projections before reconstruction of an image representation.

29 Claims, 6 Drawing Sheets

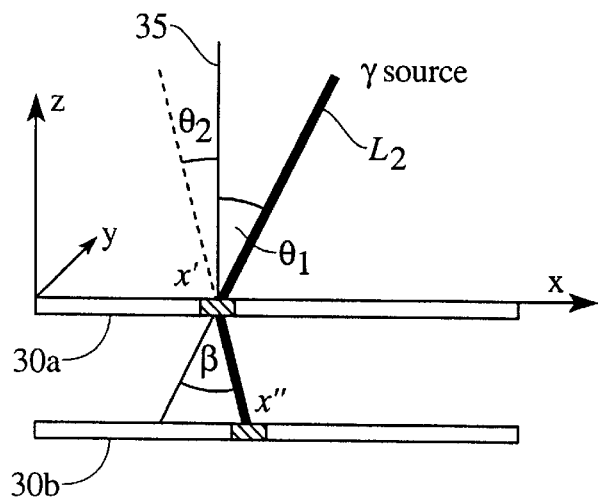
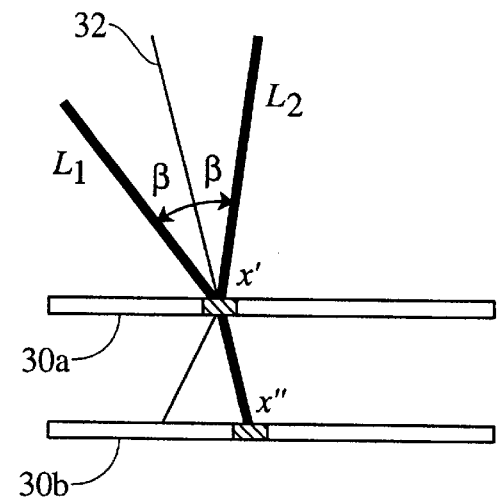
Fig. 2A          Fig. 2B
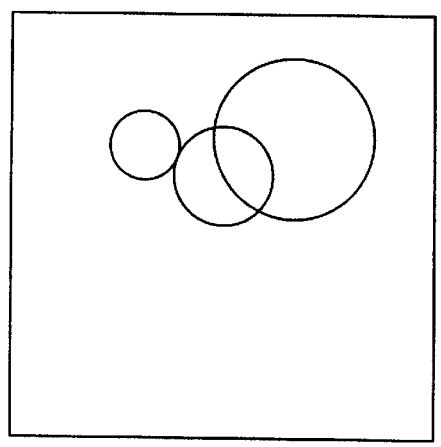
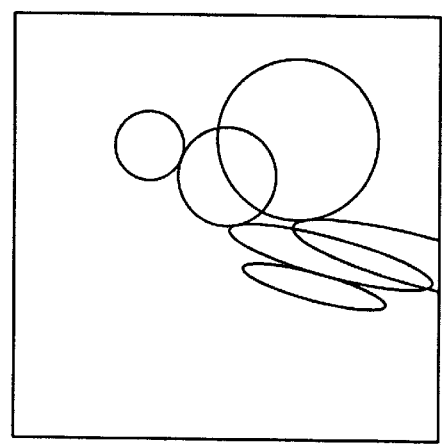
Fig. 4A          Fig. 4B

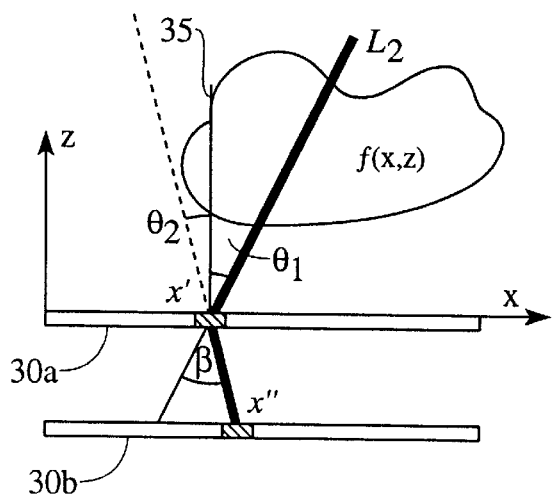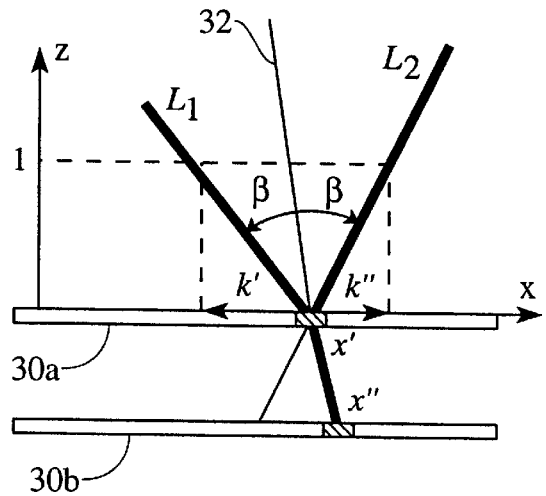
Fig. 5A          Fig. 5B
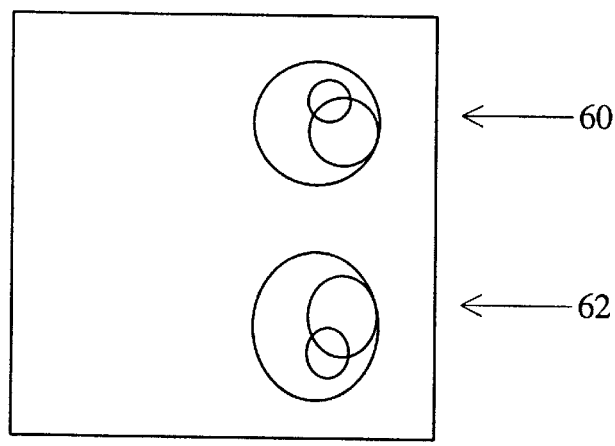
Fig. 6

IMAGE RECONSTRUCTION FROM V-PROJECTIONS ACQUIRED BY COMPTON CAMERA

BACKGROUND OF THE INVENTION

The present invention relates to the art of diagnostic imaging. It finds particular application in conjunction with nuclear or gamma cameras and will be described with particular reference thereto. It is to be appreciated, however, that the present invention will also find application in other non-invasive investigation techniques and imaging systems such as single photon planar imaging, whole body nuclear scans, positron emission tomography (PET), digital x-ray computed tomography and other diagnostic modes. It is to be further appreciated that the present invention will also find application in Compton-type telescopes used for astronomy.

Single photon emission computed tomography (SPECT) has been used to study a radionuclide distribution in a subject. Typically, one or more radiopharmaceuticals or radioisotopes are injected into a patient subject. The radioisotope preferably travels to an organ of interest whose image is to be produced. The patient is placed in an examination region of the SPECT system surrounded by large area planar radiation detectors. Radiation emitted from the patient is detected by the radiation detectors. The detectors have a mechanical collimator to limit the detector to seeing radiation from a single selected trajectory or ray, often the ray normal to the detector plane.

Typically, the detector includes a scintillation crystal that is viewed by an array of photomultiplier tubes. The relative outputs of the photomultiplier tubes are processed and corrected, as is conventional in the art, to generate an output signal indicative of (1) a position coordinate on the detector head at which each radiation event is received, and (2) an energy of each event. The energy is used to differentiate between emission and transmission radiation and between multiple emission radiation sources and to eliminate stray and secondary emission radiation. A two-dimensional projection image representation is defined by the number of radiation events received at each coordinate.

The mechanical collimator used in conventional gamma cameras, such as an Anger camera, localize the gamma emitters. This type of collimator, however, leads to low efficiency because only a fraction of the radiation passes through the collimator. Furthermore at any given time, only one view of an object of interest is obtained. Thus, the camera needs to move or rotate relative to a subject in order to collect all the data necessary for image reconstruction. Further, the collimators are fabricated of lead. Typically, each collimator is of sufficient weight that it must be connected to and removed from the head by mechanical, rather than human means. Not only is handling inconvenient, but the supporting structure for the detectors must support the detector head and hundreds of kilograms of collimator stably and without vibration.

A new type of gamma camera for SPECT relies on Compton scattering for gamma source localization and is known as a Compton camera. This camera has been proposed as an alternative to the conventional Anger camera and is advantageous because it uses electronic rather than mechanical collimation. Electronic collimation provides both high geometric efficiency and multiple image views. A proposed example of image reconstruction from data collected by a Compton camera is described in "Towards direct reconstruction from a gamma camera base on Compton scattering," by M. J. Cree and P. J. Bones, IEEE Trans. Med. Imag., Vol. 13, pp. 398–407, 1994. Although some progress has been made toward image reconstruction from a Compton camera system, at present, an acceptable filtered back-projection algorithm has proved elusive.

The present invention provides a new and improved reconstruction algorithm for a Compton camera which overcomes the above-referenced problems and others.

SUMMARY OF THE INVENTION

In accordance with the present invention, a new and improved method and apparatus for reconstructing an image representation of a region of interest of a subject including a radiation emitting source during a SPECT or nuclear camera scan is provided. A Compton camera detects the radiation emitted from the subject and generates radiation data as V-shaped projections. The V-shaped projections are converted into parallel projections and an image representation is reconstructed from the parallel projections.

In accordance with a more limited aspect of the present invention, the reconstructing includes reconstructing by filtered back projection.

In accordance with a more limited aspect of the present invention, the V-shaped projections are converted into Radon projections.

In accordance with a more limited aspect of the present invention, the Compton camera includes two radiation detectors disposed in parallel to each other.

In accordance with another aspect of the present invention, a second Compton camera is provided which is positioned at an angle, preferably a right angle, to the other Compton camera.

In accordance with another aspect of the present invention, the Compton camera includes three radiation detectors disposed in parallel to each other.

One advantage of the present invention is that image reconstruction is achievable from radiation data collected by a Compton camera.

Another advantage of the present invention is that mechanical collimators are eliminated from the diagnostic imaging system by the use of a Compton camera operating with electronic collimation.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 2A is an illustration of a two detector Compton camera detecting an incident photon from a gamma source in accordance with the present invention;

FIG. 2B illustrates a determination of a V-projection based on the detecting shown in FIG. 2A in accordance with the present invention;

FIG. 4A is an example of an image reconstructed of a selected phantom in accordance with the present invention;

FIG. 4B illustrates an image reconstructed of the selected phantom including a by-product image in accordance with the present invention;

FIG. 5A and 5B illustrate an alternative method for generating V-projections in accordance with the present invention;

FIG. 6 illustrates an image reconstructed in accordance with the method shown in FIGS. 5A and 5B including a by-product image;

DETAILED DESCRIPTION OF THE PREFERRED EMBODIMENTS

Figure 1:
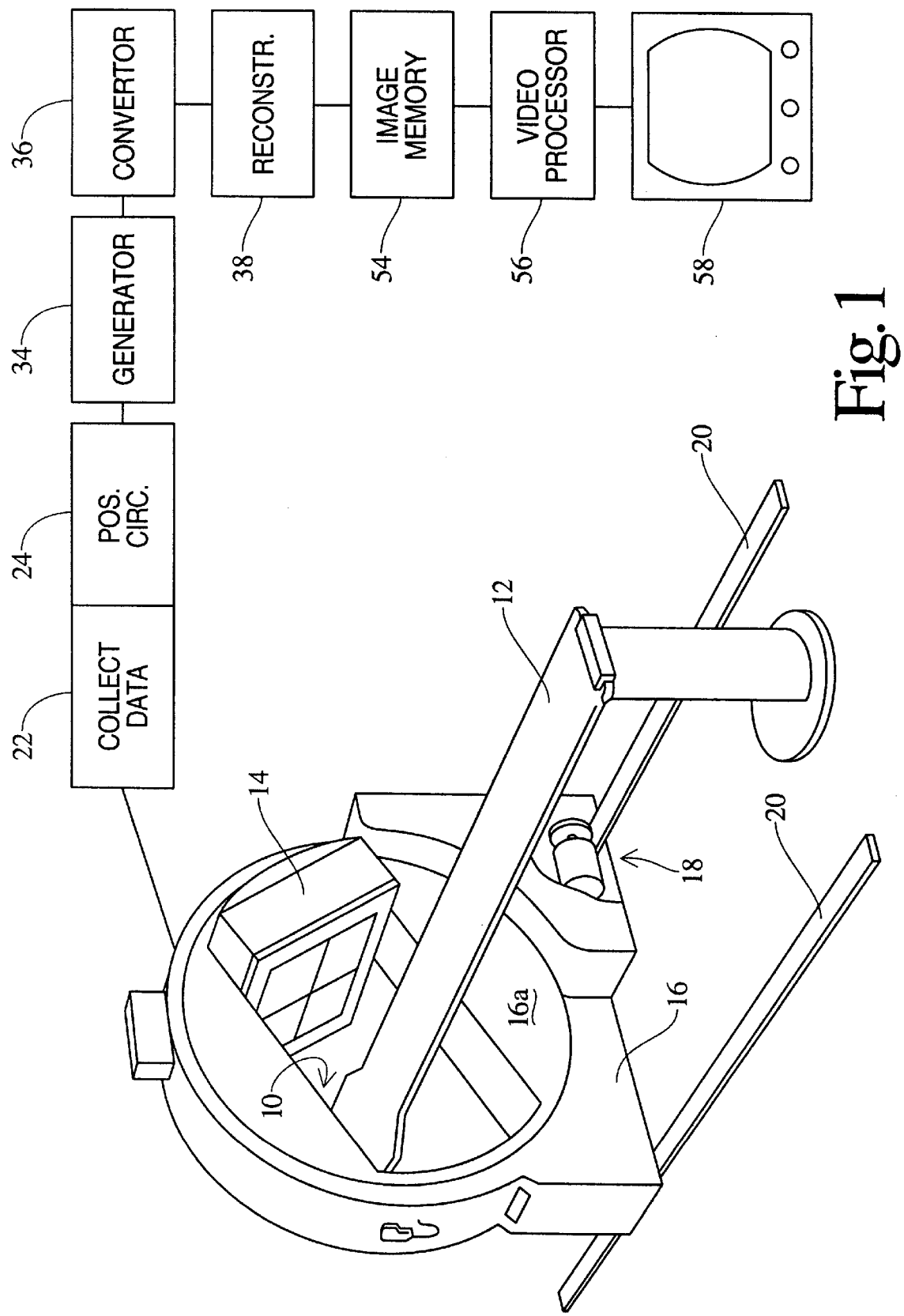
FIG. 1 is a diagrammatic illustration of a diagnostic imaging system in accordance with the present invention.

With reference to FIG. 1, a single photon emission computed tomography (SPECT) diagnostic imaging system has an examination region 10 for receiving a subject. A subject support or patient couch 12 adjustably positions the subject in the examination region 10. The examination region is viewed by a one-dimensional Compton camera 14 mounted on a gantry 16. It is to be appreciated that a greater number of cameras can be provided. The gantry includes a motor and drive assembly 18 which moves the gantry along tracks 20 so that selected regions of the subject may be imaged. The motor and drive assembly 18 also selectively rotates a rotatable portion 16a of the gantry and camera 14 around the subject such that selected views can be imaged by the camera 14.

In the preferred embodiment, the camera 14 includes two linear radiation detectors each having a scintillation crystal that is viewed by an array of photomultiplier tubes. Radiation emanating from radiopharmaceuticals or other gamma radiation producing substances injected into the subject follows linear paths or rays outlined in radial directions from an isotope of the injected substance through the examination region 10 with radiation along a fraction of the rays being detected by the camera 14. Each time a radiation event occurs, radiation striking the scintillation crystal causes a light flash or scintillation. The photomultiplier tubes nearest the scintillation respond with proportional output signals. The gantry 16 or an associated control console includes a data collection processor 22 for processing the data collected by the detector 14. Position and energy resolving circuitry 24 connected to the photomultiplier tubes determine the energy and position, of each scintillation.

With reference to FIGS. 2A and 2B, the Compton camera 14 is a one-dimensional camera which includes first and second radiation detectors or planes 30a and 30b disposed in parallel to each other and facing the examination region which contains a gamma source. For exemplary purposes, a photon emanating from the gamma source follows a path $L_2$ and strikes the first detector 30a at a position x'. The photon undergoes Compton scattering in the first detector 30a and is absorbed by the second detector 30b at a position x". In other words, the path of the photon is changed or deflected by an angle β upon striking the first detector. This angle β is referred to as a scattering or Compton angle.

The detectors 30a and 30b determine the energy values deposited by the photon at positions x' and x" and calculate the energy difference or energy loss ΔE during scattering. With the initial energy E and energy loss ΔE and using a Compton formula:

$$\cos\beta = 1 - \frac{mc^2 \Delta E}{(E - \Delta E)E}, \quad (1)$$

the scattering angle β is determined. Once the values of x', x" and β are known, a gamma source location of the photon is limited by a cone framed by two semilines $L_1$, $L_2$ which converge to form a vertex on the first detector 30a at position x'. The semilines $L_1$, $L_2$ define a cone area in which possible locations of the gamma source reside.

With further reference to FIG. 2B, the semilines $L_1$, $L_2$ define a V-shape, where each line $L_1$ and $L_2$ form an angle from a central dividing line 32 of the defined cone which is equal to the scattering angle β. A projection data generator 34 generates projection data represented by a function q(x', x", β) of the three variables whose values are equal to a sum of two integrals along the semilines $L_1$ and $L_2$ weighted by cosines of incident angles $\theta_1$ and $\theta_2$ defined between a normal 35 to the detectors intersecting at position x' and lines $L_1$ and $L_2$. The function q(x', x", β) is represented by $$q(x', x'', \beta) = |\cos\theta_1| \int_{L_1} f(x, z) dl + |\cos\theta_2| \int_{L_2} f(x, z) dl. \quad (2)$$

It is to be appreciated that other integrals along the semilines $L_1$ and $L_2$ may be obtained. The function q(x', x", β) is defined on a three-dimensional manifold and is referred to as a V-transform of (x,z) and its value q(x', x", β) at the point (x',x", β) is referred to as a V-projection which is a three-dimensional projection. The name is derived from its V-shape defined by the semilines $L_1$ and $L_2$.

Figure 3:
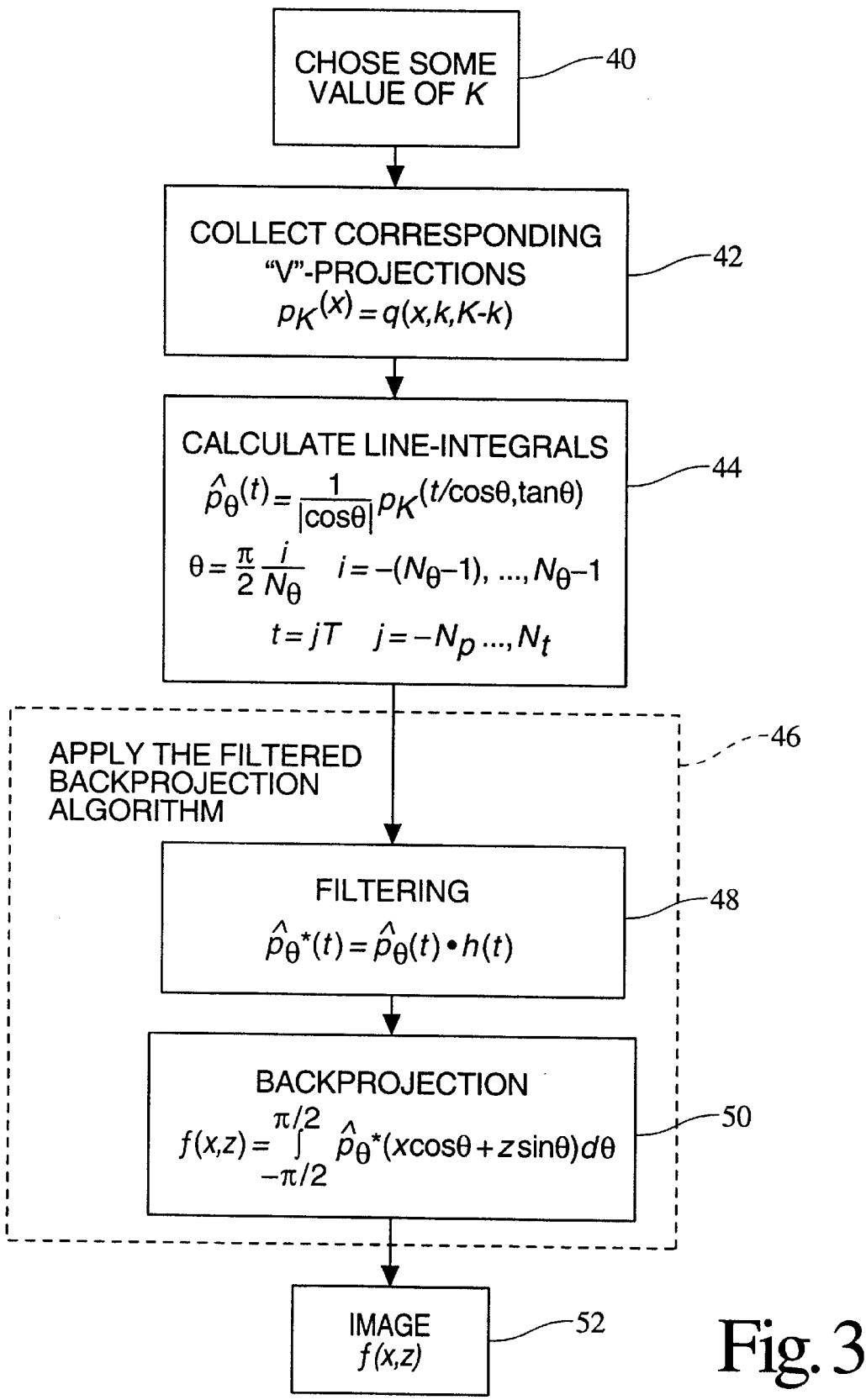
FIG. 3 illustrates a method of image reconstruction from a V-projection in accordance with the present invention.

With reference to FIGS. 1 and 3, a conversion processor 36 and a reconstruction processor 38 convert and reconstruct the V-projection data into an image representation. Once multiple V-projections are generated, they are grouped in a three-dimensional set. The three-dimensional set is subdivided into two-dimensional subsets $S_K$ specified by a selection parameter K at 40 in such a way that data in each subset is viewed as line integrals of an image f(x,z):

$$f_k(x, z) = \begin{cases} f(x, z) & \text{if } z \geq 0 \\ f(x + Kz, -z) & \text{if } z < 0 \end{cases}. \quad (3)$$

Any value of K is selected, for example 1.5, 2.2, etc... and the corresponding V-projections $p_K(x)$ are collected 42 as:

$$p_K(x) = q(x, k, K-k) \quad (4)$$

The subsets $S_K$ represent a transformation of the region of interest. In order to reconstruct an image representation of the region of interest, the V-transform is converted into an equivalent transform of parallel projections. In the preferred embodiment, the V-transform is converted to a Radon transform. The line integrals $p_\theta(t)$ are calculated 44, for example, as follows:

$$\hat{p}_\theta(t) = \frac{1}{|\cos\theta|} p_K(t/\cos\theta, \tan\theta). \tag{5}$$

$$\theta = \frac{\pi}{2} \frac{i}{N_\theta} \quad i = -(N_\theta - 1), \ldots, N_\theta - 1$$

$$t = jT \quad j = -N_t, \ldots, N_t.$$

Assuming that the detectors have infinite size, the V-transform $q(x', x'', \beta)$ considered on any one subset $S_K$ for points $(x', x'', \beta) \in S_K$, is equivalent to a Radon transform of $f_K(x,z)$. With the Radon transform, reconstruction of an image representation of the region of interest is achievable using data from one subset $S_K$ with a conventional reconstruction algorithm, for example, an iterative algorithm, a radon inversion algorithm, or any tomographic reconstruction algorithm.

In a preferred embodiment, a filtered back projection algorithm 46 is used as shown in FIG. 3. The above calculated line-integrals $\hat{p}$ from equation (5) are filtered 48 with a filter h(t) to generated filtered line integrals $\hat{p}^*$ as:

$$\hat{p}_\theta^*(t) = \hat{p}_\theta(t) \otimes h(t) \tag{6}$$

where $\otimes$ represents a convolution operation. Then a back-projection 50 is applied, for example, by:

$$f(x, z) = \int_{-\pi/2}^{\pi/2} \hat{p}_\theta L^*(x\cos\theta + z\sin\theta) d\theta \tag{7}$$

and an image 52 is reconstructed. The reconstruction image f(x,z) is stored in an image memory 54 which a video processor 56 may selectively access and process selected portions of an image into a human readable form such as on a video display 58.

For exemplary purposes, a desired image representation of a region of interest is shown in FIG. 4A which would result by reconstructing directly measured and calculated transformations. However, due to the conversion from the measured V-transform to a Radon transform, the reconstruction produces an additional by-product image in which, for example, the desired image structures cast artifact shadows, as seen in the bottom half of FIG. 4B. The desired image of the region of interest is reconstructed in the upper half of the plane represented by f(x,z) of Equation (3); whereas, the lower half of the plane contains a by-product represented by f(x+Kz, −z) of Equation (3). The by-product can be described as a mirrored shear transformation of the desired image and can be disregarded or deleted from the resultant image. The by-product image may also be described as a shadow of the desired image. Although one set of data $S_K$ may be sufficient for performing a full reconstruction, more than one data set may be used to reduce errors.

In a second embodiment alternative to the first, the radiation detectors have a finite size. With finite size detectors, V-projections in any subset $S_K$ represent only part of the full Radon transform of $f_K(x,z)$. To compensate this deficiency, the camera may be rotated around the subject to collect multiple projection data which is converted and reconstructed in a similar manner as described above.

With reference to FIGS. 5A and 5B, an alternative method of generating V-projections is shown two dimensionally for simplicity of illustration. An incident photon traveling along path $L_2$ undergoes Compton scattering in the first detector 30a, and is absorbed by the second detector 30b. The corresponding positions x' and x'' of the contact points on each detector and the scattering angle β are measured. If x', x'' and β are known, the source location of the photon is limited by two semilines $L_1$ and $L_2$ which converge to a common vertex on the front detector 30a at position x' as shown in FIG. 5B. The data collected by the camera are used to generate V-projections which are represented by a function q(x',k', k''). The values k' and k'' are determined as unit projections of semilines $L_1$, $L_2$ along the x-axis which gives a selected y-axis value for semilines $L_1$ and $L_2$. A z-axis value of 1 or unity is shown.

The relationship between gamma source f(x,z) and the V-projections is given by $$q(x', k', k'') = \int_0^\infty f(x' + k'z, z)dz + \int_0^\infty f(x' + k''z, z)dz. \tag{8}$$

The V-projection q(x,k,−k/K) is equal to a line projection $p_K(x,k)$ of the $K^{th}$ set onto the x-axis as:

$$p_K(x, k) = \int_{-\infty}^\infty f_K(x + kz, z)dz. \tag{9}$$

The function $f_K(x,z)$ of the relationship between the gamma source in the $K^{th}$ set is defined as $$f_K(x, z) = \begin{cases} f(x, z) & \text{if } z \geq 0 \\ Kf(x - Kz) & \text{if } z < 0 \end{cases} \tag{10}$$

If detectors have infinite size, then for any fixed K, $f_K(x,z)$ can be reconstructed from subset $S_K = \{q(x', k', k'')/k'' = -Kk'\}$ of the projection data. An example of an image representation reconstructed with this method is shown in FIG. 6. A desired image representation 60 of the object reconstructed appears in the upper right corner while a by-product image 62 appears in the lower right corner. Infinite detectors can be avoided if two cameras are used to collect projection data which is the subject of the following third embodiment.

Figure 7:
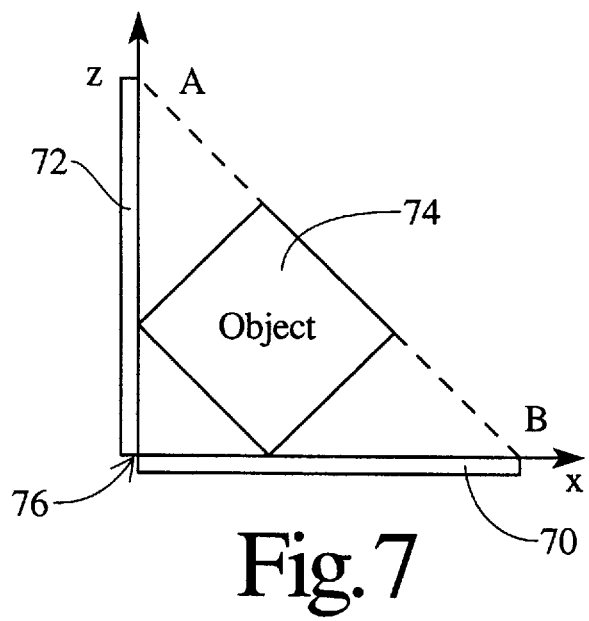
FIG. 7 illustrates a third embodiment of the present invention which includes two Compton cameras disposed at a 90° angle to each other.

In a third embodiment and with reference to FIG. 7, the diagnostic imaging system includes multiple one-dimensional Compton cameras 70 and 72 positioned around an object 74 to collect projection data. As shown in FIG. 7, two Compton cameras 70, 72 each include a plurality of linear radiation detectors of finite extent disposed in parallel to each other, for example, as shown in FIG. 2A or FIG. 9C. The two cameras are positioned at right angles to each other along the x and z axes, respectively for simplicity of calculation. Of course, other angular configurations can be used. The radiation detectors extend in each camera 70, 72 from the origin 76 of the x-z axis in a positive direction while the object 74 to be imaged is placed in the first quadrant of the x-z plane so as to be viewed by both cameras. The detectors collect radiation data which is used to generate V-projections from each detector as described in the first embodiment.

Before reconstructing the V-projections, a combination of two V-projections are selected, one from each camera 70 and 72, and the conversion processor 36 or function transforms the V-projections into corresponding parallel projections in a manner previously described. Preferably, the parallel projections are Radon projections which are equivalent to a line-integral f(x,z) of the original object 74 combined with three virtual images or by-product images of the original object. Once the parallel projections are obtained, a reconstruction processor reconstructs an image representation based on the parallel projections using, for example, a conventional filtered backprojection algorithm. The additional by-products or virtual images of the original object may be generated as a result of the transformation/ conversion of the measured and calculated V-projections to estimated parallel projections.

Figure 8:
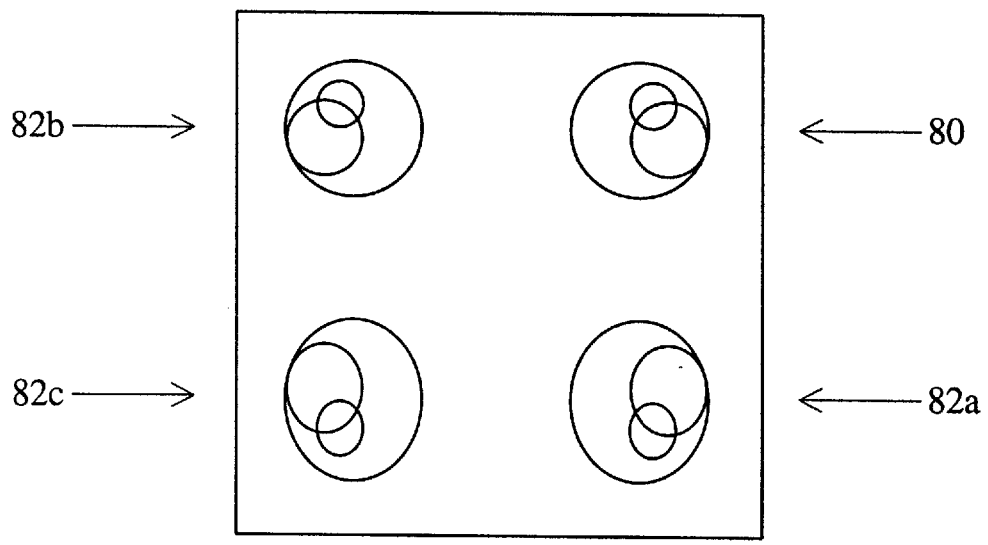
FIG. 8 illustrates an image representation of an object reconstructed by data collected from the apparatus shown in FIG. 7.

With reference to FIG. 8, an example of an image representation of the object 74 is shown after reconstruction using the two Compton cameras 70 and 72. A desired image representation 80 of the original object is shown in the first quadrant (upper right corner) and three virtual objects 82a, 82b and 82c are shown in the other three quadrants. The virtual objects are regarded as a by-product image which can be disregarded or removed from the resultant image. The virtual objects 82a, 82b, and 82c are related to the desired image 80 by reflection and/or compression about the x-z axis. A compression coefficient depends on the particular subset of the V-projections used for reconstruction.

A minimum size of each detector within the cameras 70 and 72 needed to obtain a full set of line integrals is determined based on the object size as shown by dotted line AB in FIG. 7. Reconstruction of the original object 74, as well as the virtual objects, is performed using a subset of the V-projection data using a conventional filtered back projection algorithm.

For the two-dimensional detectors in the previous embodiments, a collimator is preferably mounted on a radiation receiving face of the camera to collimate the detected radiation in a trans-sectional direction. For example, the collimator includes an aperture or slit to detect a slice perpendicular to the z-direction. Alternately, a very thin scanning detector is used to force the detection to be in a slice perpendicular to the z-direction.

Figure 9A:
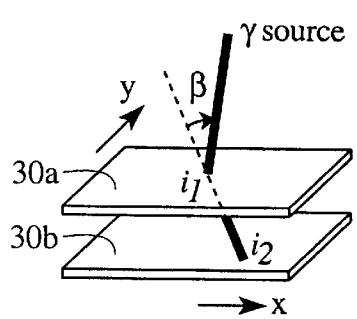
FIG. 9A, 9B and 9C illustrate a fourth embodiment of the present invention which includes a Compton camera having three linear detectors.
Figure 9B:
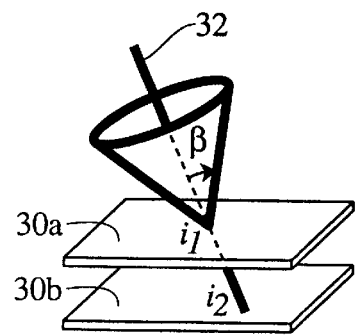
Figure 9C:
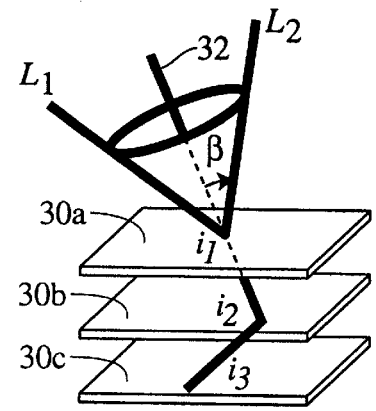

With reference to FIGS. 9A, 9B and 9C, a fourth embodiment is shown. As described in the above embodiments, image reconstruction is performed from V-projections acquired by a Compton camera having two gamma detectors 30a and 30b as seen in FIGS. 9A and 9B. Two vertex electronic collimation is performed by coincident registration of two interaction events $i_1$ and $i_2$ which occur when incident gamma photons undergo Compton scattering in a first detector 30a and are absorbed in the second detector 30b. The interaction events $i_1$ and $i_2$ have coordinate positions $(x_1, y_1)$ and $(x_2, y_2)$ respectively on the first and second detector planes 30a and 30b. The two interaction events $i_1$ and $i_2$ along with the scattering angle $\beta$ are used to define a "cone of possibility" to determine the location of the origin of a particular gamma photon.

FIG. 9C illustrates an example of the Compton camera having a third radiation detector 30c operating by three vertex electronic collimation which is achieved by coincident registration of three interaction events $i_1$, $i_2$ and $i_3$ at points $(x_1, y_1)$, $(x_2, y_2)$ and $(x_3, y_3)$ respectively. The interaction events include Compton scatterings in the first two detectors 30a and 30b closest to the gamma source and absorption in the third detector 30c furthest from the source. Polarization occurs in this process such that the plane containing the three vertices $i_1$, $i_2$ and $i_3$ form a small angle with respect to the plane containing the gamma source point and the first two vertices $i_1$ and $i_2$. In other words, the four points (the source and three vertices) are roughly coplanar. As a result, the "cone uncertainty" is reduced, and the gamma source location is approximated by two semilines L and L' defining a "V" shape. The semilines $L_1$ and $L_2$ are a result of the intersection between the cone and the plane containing the vertices at the coordinates of $i_1$, $i_2$ and $i_3$. With the three vertex collimation, mechanical collimation is not required.

A relationship between a three-dimensional gamma source distribution $f(x,z)$ and a rate of photon counting $q(i_1, i_2)$ for specific values of $i_1$, $i_2$, $\beta$ is given by $$q(i_1, i_2, \beta) \propto \int_{\text{cone}} f(x, z) da. \quad (11)$$

Data acquired by the camera can be considered as samples of $q(i_1, i_2, \beta)$ and are called cone projections or V-projections.

Full three dimensional image reconstruction from "V"-projections is achieved by extending the methods previously described for a one-dimensional Compton camera.

Figure 10:
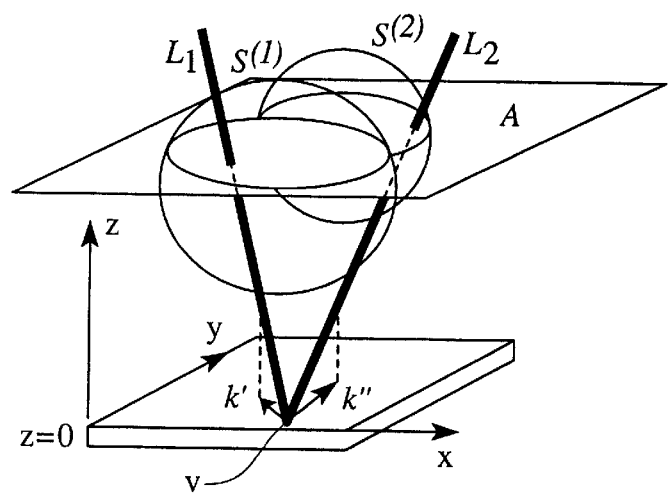
FIG. 10 illustrates a V-projection obtained from the detectors illustrated in FIG. 9C based on a two sphere phantom being imaged.

With reference to FIG. 10, consider three-dimensional space with (x,y,z) coordinates and a gamma source distribution described by a function $f(x,z)$ for $z \geq 0$ (hereinafter, bold notation represents two-dimensional vectors and points lying in the x-y plane). An arbitrary "V"-projection defined by the two semilines $L_1$, $L_2$ with common vertex on z=0 plane may be specified by a point v and two vectors k' and k" on the x-y plane. Thus, the data acquired by the camera can be represented by a function q(v,k',k"). A relationship between the gamma source $f(x,z)$ and projection data q(v, k',k") is described by:

$$q(v', k', k'') = \int_0^\infty f(x + k'z, z)dz + \int_0^\infty f(x + k''z, z)dz. \quad (12)$$

Image reconstruction is based on a mapping between "V"-projections and line-projections as described above for two-dimensional imaging. The mapping is realized by introducing a function:

$$f_K(x, z) = \begin{cases} f(x, z) & \text{if } z \geq 0 \\ f(x + Kz, -z) & \text{if } z < 0 \end{cases}. \quad (13)$$

The "V"-projection q(v,k,K'-k) of the function $f(x,z)$ for $z \leq 0$ is equal to a line projection $p_K$ as:

$$p_K(x, k) = \int_R f_K(x + kz, z)dz \quad (14)$$

of the function $f_K(x,z)$. Since $f_K(x,z)$ is equivalent to the function $f(x,z)$ in the region of interest ($z \geq 0$), the image can be reconstructed by applying a filtered backprojection algorithm to a subset $S_K$ of "V"-projections $$S_K = \{q(v,k',k'') | \text{for } K = k' + k''\}. \quad (15)$$

Figure 11:
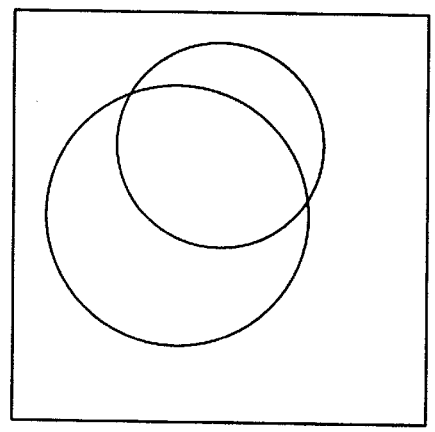
FIG. 11 illustrates an image representation reconstructed based on the V-projections obtained as shown in FIG. 10.

With further reference to FIG. 10, computer simulations of the above-described image reconstruction method and system were performed with a phantom including two spheres $S^{(1)}$ and $S^{(2)}$ where sphere $S^{(2)}$ has twice the intensity of sphere $S^{(1)}$. A result of image reconstruction of a horizontal slice A from a subset so of generated V-projections is shown in FIG. 11.

Alternatively, two Compton cameras each operating with three detector planes are disposed at an angle to each other, for example, a right angle as described in the third embodiment.

It is to be appreciated that the present invention finds application with telescoping systems which image distant objects based on energy distributions. An example includes a Compton telescope used in astronomy.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A method of generating an image representation of a region of interest of a subject having radiation emitted therefrom, the radiation being detected by a first Compton camera, the method comprising:

collecting radiation data from the detected radiation as a v-shaped projection defined by converging lines;

converting the v-shaped projection into a parallel projection; and reconstructing an image representation from the parallel projection.

2. The method of generating an image representation as set forth in claim 1 further including:

providing at least first and second radiation detectors for collecting the radiation data, the first radiation detector being disposed between the subject and the second radiation detector and being parallel to the second radiation detector, the detected radiation undergoing Compton scattering in the first radiation detector;

determining detection positions of a photon detected on the first and second radiation detectors;

determining an energy deposited by the photon on both the first and second radiation detectors at the detection positions; and determining the v-shaped projection based on the detection positions and the energy determined on both the first and second radiation detectors.

3. The method of generating an image representation as set forth in claim 1 further including providing a second Compton camera having a plurality of radiation detectors for collecting radiation data, the first and second Compton cameras being disposed at a fixed angle to each other and the subject being positioned so as to be viewed by both Compton cameras.

4. The method of generating an image representation as set forth in claim 3 further including:

generating v-shaped projections from the radiation data collected from both the first and second Compton cameras;

selecting a combination of the v-shaped projections from both the first and second Compton cameras where at least one v-shaped projection selected being generated from the first Compton camera and at least one v-shaped projection selected being generated from the second Compton camera; and converting the selected v-shaped projections to parallel projections.

5. The method of generating an image representation as set forth in claim 1 further including:

providing three radiation detectors disposed in parallel to each other for detecting radiation emitted from the subject, the radiation exhibiting Compton scattering in at least one of the three radiation detectors and being absorbed in another of the three radiation detectors; and collecting radiation data as the v-shaped projection based on corresponding radiation detected on each of the three radiation detectors.

6. The method of generating an image representation as set forth in claim 5 further includes reconstructing a three-dimensional image representation of a region of interest from the subject based on the v-shaped projection.

7. The method of generating an image representation as set forth in claim 1 wherein the converting includes converting the v-shaped projection into a Radon projection to obtain the parallel projection.

8. The method of generating an image representation as set forth in claim 1 wherein the reconstructing includes generating an image representation of the region of interest and a by-product image of the region of interest.

9. The method of generating an image representation as set forth in claim 8 further including deleting the by-product image.

10. The method of generating an image representation as set forth in claim 1 further including selectively rotating the Compton camera around the subject.

11. The method of generating an image representation as set forth in claim 1 further including:

collecting a plurality of v-shaped projections from the detected radiation; and converting a selected subset of the plurality of v-shaped projections into parallel projections.

12. The method of generating an image representation as set forth in claim 1 wherein the reconstructing includes filtered back projection.

13. A diagnostic imaging system for reconstructing an image representation of a subject including a first plurality of radiation detectors parallelly disposed to each other for detecting radiation from an examination region, and producing electrical data indicative of coordinate locations and energy values on each of the radiation detectors at which radiation is detected, the radiation detected being scattered by at least one of the radiation detectors at a scattering angle, and a reconstruction processor reconstructs an image representation, the diagnostic imaging system comprising:

a projection processor for determining the scattering angle based on the energy values of the received radiation on the first plurality of radiation detectors and generating divergent projection data defined by (i) a vertex at a location where the radiation is detected on a first radiation detector of the first plurality of radiation detectors nearest the examination region, and (ii) the scattering angle; and a conversion processor for converting the divergent projection data to parallel projection data which the reconstruction processor reconstructs into an image representation.

14. The diagnostic imaging system as set forth in claim 13 wherein the reconstruction processor reconstructs the image representation by filtered back projection.

15. The diagnostic imaging system as set forth in claim 13 wherein the projection processor defines two divergent semilines which converge at the vertex of the projection data forming an angle therebetween of twice the scattering angle, and the conversion processor includes a means for calculating integrals along the semilines to generate corresponding parallel projection data.

16. The diagnostic imaging system as set forth in claim 13 wherein the first plurality of radiation detectors include three radiation detector planes disposed in parallel to each other and the projection processor generates the divergent projection data based on the radiation detected on each of the three radiation detector planes.

17. The diagnostic imaging system as set forth in claim 16 wherein the reconstruction processor generates a three-dimensional image representation based on the divergent projection data generated from the radiation detected on each of the three radiation detector planes.

18. The diagnostic imaging system as set forth in claim 13 further including a second plurality of radiation detectors for detecting radiation from the examination region and producing electrical data indicative of coordinate locations and energy values on each of the second plurality of radiation detectors at which radiation is detected, the radiation detected being scattered by at least one of the second plurality of radiation detectors at a scattering angle, the second plurality of radiation detectors being disposed at a selected angle to the first plurality of radiation detectors, the projection processor generating second divergent projection data based on the radiation detected by the second plurality of radiation detectors.

19. The diagnostic imaging system as set forth in claim 18 wherein the conversion processor generates the parallel projection data from the divergent projection data from both the first and second pluralities of radiation detectors.

20. A method of generating an image representation of a region of interest of a subject by a SPECT diagnostic imaging system where the subject is injected with a radiation source, the method comprising:

detecting a photon from the radiation source at a first position on a first radiation detection plane and scattering the photon at a scattering angle;

detecting the scattered photon at a second position on a second radiation detection plane, the second radiation detector plane being parallel to the first radiation detection plane;

determining two lines which intersect at the first position on the first radiation detection plane which diverge in accordance with the scattering angle, a source of the photon lying along one of the lines;

generating a three-dimensional set of projection data based on integrals taken along the two lines;

dividing the three-dimensional set of projection data into a plurality of two-dimensional subsets of projection data such that one subset defines an equivalency with a line integral of the region of interest; and reconstructing the one subset of projection data into an image representation of the region of interest of the subject.

21. The method of generating an image representation as set forth in claim 20 further including determining photon energy values at both the first and second positions.

22. The method of generating an image representation as set forth in claim 20 wherein the reconstructing includes reconstructing a desired image representation of the region of interest of the subject and a by-product, mirrored shear image of the desired image representation.

23. The method of generating an image representation as set forth in claim 20 wherein the generating projection data includes:

determining a plurality of integrals along the lines; and combining the plurality of integrals to form the three-dimensional set of projection data.

24. The method of generating an image representation as set forth in claim 20 wherein the step of dividing the set of projection data includes generating an equivalent Radon transform of the projection data.

25. The method of generating an image representation as set forth in claim 20 further including:

detecting a second photon of radiation at a first position on a third radiation detection plane disposed at a right angle to the first radiation detection plane and scattering the photon;

detecting the scattered photon from the third radiation detection plane at a fourth radiation detection plane parallel to the third radiation detection plane; and generating the three dimensional set of projection data based on the photons detected at the first, second, third and fourth radiation planes.

26. An image reconstruction assembly which generates an image representation of an object including a gamma source, the assembly comprising:

radiation detecting means for detecting radiation received from the gamma source by electronic collimation and collecting radiation data based on the radiation detected;

a means for generating divergent projection data from the radiation data collected;

a means for transforming the divergent projection data into parallel projection data; and a reconstruction processor which reconstructs the parallel projection data into an image representation.

27. The image reconstruction assembly as set forth in claim 26 wherein the generating means generates the divergent projection data based on two lines forming a v-shape having a vertex on the radiation detecting means, the two lines being determined by locations of detected radiation by the radiation detecting means and energy deposited at the locations, the locations being related by a scatter angle, the two lines defining an area for locating the gamma source.

28. The image reconstruction assembly as set forth in claim 26 wherein the radiation detecting means includes a first, second, and third radiation detectors, the first detector being disposed nearest to the gamma source, the third detector being disposed furthest from the gamma source and the second detector being disposed between the first and third detectors such that a photon from the gamma source detected by the first radiation detector undergoes scattering in the first and second detectors and the third detector absorbing the photon.

29. The image reconstruction assembly as set forth in claim 26 wherein the radiation detecting means includes first and second Compton cameras disposed at a right angle to each other.

* * * * *